United States Patent
Keggenhoff et al.

(10) Patent No.: US 7,312,362 B2
(45) Date of Patent: Dec. 25, 2007

(54) PROCESS FOR THE PRODUCTION OF DI- AND POLYAMINES OF THE DIPHENYLMETHANE SERIES

(75) Inventors: Berthold Keggenhoff, Krefeld (DE); Richard Adamson, Leichlingen (DE); Rudolf Uchdorf, Shanghai (CN); Fritz Pohl, Brunsbüttel (DE)

(73) Assignee: Bayer MaterialScience AG, Leverkusen (DE)

( * ) Notice: Subject to any disclaimer, the term of this patent is extended or adjusted under 35 U.S.C. 154(b) by 0 days.

(21) Appl. No.: 11/657,338

(22) Filed: Jan. 24, 2007

(65) Prior Publication Data

US 2007/0179317 A1    Aug. 2, 2007

(30) Foreign Application Priority Data

Jan. 28, 2006    (DE) .................. 10 2006 004 041

(51) Int. Cl.
*C07C 209/24* (2006.01)
(52) U.S. Cl. ..................................... 564/397
(58) Field of Classification Search ............ None
See application file for complete search history.

(56) References Cited

U.S. PATENT DOCUMENTS

| | | | |
|---|---|---|---|
| 4,792,624 A | 12/1988 | Hatfield, Jr. et al. | 564/333 |
| 5,053,539 A | 10/1991 | Yano et al. | 564/333 |
| 5,286,760 A | 2/1994 | Bolton et al. | 521/160 |
| 6,433,219 B1 | 8/2002 | Ströfer et al. | 560/347 |
| 6,576,788 B1 | 6/2003 | Penzel et al. | 560/333 |
| 6,639,102 B2 | 10/2003 | Hagen et al. | 560/347 |
| 6,831,192 B2 | 12/2004 | Ströfer et al. | 560/347 |
| 2002/0132953 A1 | 9/2002 | Strofer et al. | 528/44 |
| 2003/0176626 A1 | 9/2003 | Hagen et al. | 528/310 |
| 2005/0014975 A1 | 1/2005 | Strofer et al. | 564/330 |

FOREIGN PATENT DOCUMENTS

| | | |
|---|---|---|
| DE | 844 896 | 9/1952 |
| GB | 1 517 585 | 7/1978 |

*Primary Examiner*—Samuel A. Barts
(74) *Attorney, Agent, or Firm*—Lyndanne M. Whalen; John E. Mrozinski, Jr.

(57) ABSTRACT

The present invention relates to a process for the production of mixtures of di- and polyamines of the diphenylmethane series (MDA) containing less than 1,000 ppm of water and less than 200 ppm of aniline by reaction of aniline and formaldehyde in the presence of acid catalysts and subsequent separation of the acid catalyst and subsequent distillative separation of water and aniline in an at least a two-stage distillation including a flash evaporation and subsequent cooling.

5 Claims, 2 Drawing Sheets

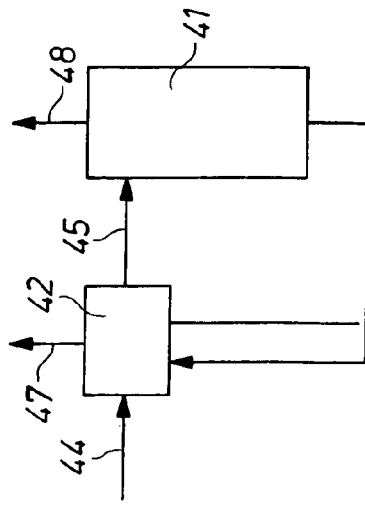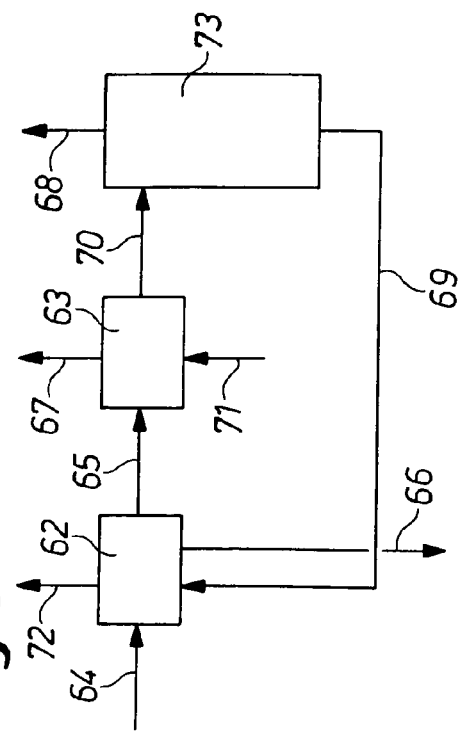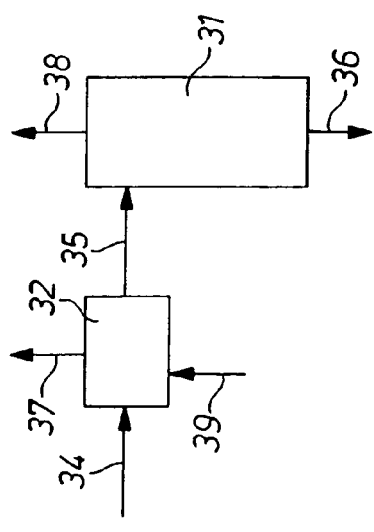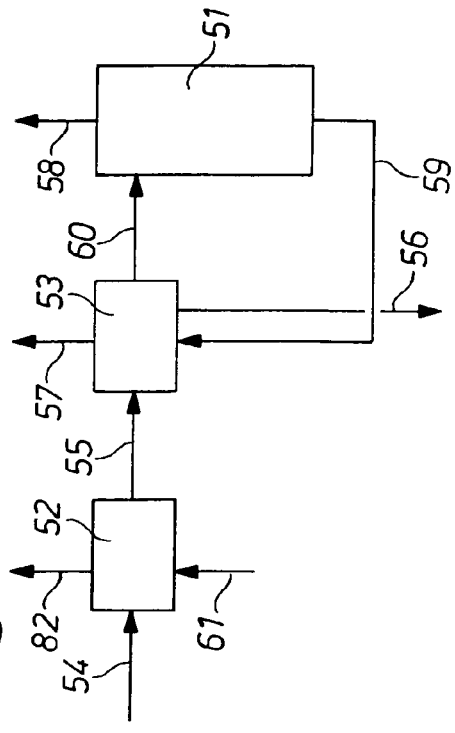

PROCESS FOR THE PRODUCTION OF DI- AND POLYAMINES OF THE DIPHENYLMETHANE SERIES

FIELD OF THE INVENTION

The present invention relates to a process for the production of mixtures of di- and polyamines of the diphenylmethane series containing less than 1,000 ppm of water and less than 200 ppm of aniline by reaction of aniline and formaldehyde in the presence of acid catalysts and subsequent separation of the acid catalyst and subsequent distillative separation of water and aniline in an at least two-stage distillation including a flash evaporation and subsequent cooling.

BACKGROUND OF THE INVENTION

The production of mixtures of di- and polyamines of the diphenylmethane series (MDA) with the principal component diaminodiphenylmethane (diamines) by reaction of aniline with formaldehyde in the presence of acid catalysts is generally known. The di- and polyamine mixtures are widely used predominantly for the production of the corresponding di- and polyisocyanate mixtures. Examples for continuous or partially discontinuous processes are disclosed in U.S. Pat. No. 5,286,760, EP-A-451442 and WO-A-99/40059. Therein it is in fact mentioned that after neutralization of the acid reaction mixture, phase separation and optionally washing with water, adhering water and excess aniline is removed distillatively, normally under vacuum. These disclosures do not however give any indication of the significance of the contents of water and aniline for the further use of the di- and polyamines for the production of the corresponding di- and polyisocyanates. Also, in the literature no processes for achieving these low contents of water and aniline are described. Also there is no indication in the literature of how the distillation of the di- and polyamines with separation of aniline and water can be energetically optimized. A further problem area is the return of the separated aniline to the reaction, wherein according to EP-A-0283757 as far as possible no MDA should be returned to the reaction with formaldehyde.

SUMMARY OF THE INVENTION

It has now been found that low contents of water and aniline in the di- and polyamines of under 1,000 ppm water and under 200 ppm aniline is an important condition for processing to the corresponding di- and polyisocyanates with low contents of by-products. Because higher contents of water and aniline in the di- and polyamines lead in the process for the isocyanate production to secondary reactions, e.g. to elevated contents of iron and low-boiling isocyanates which for their part lead to the formation of chlorine-containing impurities. It has furthermore been found that these very low contents of water and aniline can be obtained by a specially coordinated sequence of distillation steps and preferably using the heat of the di- and polyamines obtained containing less than 1,000 ppm of water and less than 200 ppm of aniline. The aniline recovered as distillate thereby contains, after separation of water has been carried out, preferably less than 0.5 wt. % of di- and polyamines. In addition, external heat, preferably steam at an absolute pressure of 6 bar or less can also optionally be used, and thus with low primary energy use a stable process control be achieved. It has further been found that the di- and polyamines again split off aniline on storage at high temperatures, particularly above 150° C., so that cooling of the product after distillation is essential to achieve the quality.

BRIEF DESCRIPTION OF THE FIGURES

The present invention will now be described for purposes of illustration and not limitation in conjunction with the figures, wherein:

FIG. 3 shows a process flowchart of a two-stage distillation including a flash evaporation with feed of additional external energy;

FIG. 4 illustrates a process flowchart of a two-stage distillation using a flash evaporation with feed of waste heat from the distillation;

FIG. 5 depicts a process flowchart of a three-stage distillation including a flash evaporation with feed of additional external energy and with feed of waste heat from the distillation; and FIG. 6 shows a process flowchart of a three-stage distillation using a flash evaporation with feed of waste heat from the distillation and with feed of additional external energy.

DETAILED DESCRIPTION OF THE INVENTION

Figure 1:
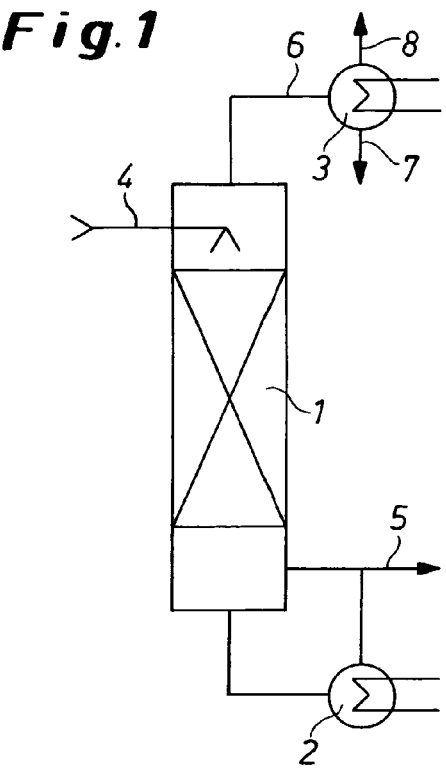
FIG. 1 shows a process flowchart of a single-stage distillation.

The present invention will now be described for purposes of illustration and not limitation. Except in the operating examples, or where otherwise indicated, all numbers expressing quantities, percentages, and so forth in the specification are to be understood as being modified in all instances by the term "about.".

The present invention provides a simple process, which can be operated with low energy consumption, for the production of di- and polyamines of the diphenylmethane series thereby allowing production of the corresponding di- and polyisocyanates by subsequent phosgenation with reduced formation of by-products.

The present invention provides a process for the production of di- and polyamines of the diphenylmethane series involving the following steps:

a) reacting aniline and formaldehyde in the presence of an acid catalyst resulting in a reaction mixture containing di- and polyamines;

b) neutralizing the reaction mixture containing di- and polyamines;

c) separating the neutralized reaction mixture containing di- and polyamines into an organic phase containing di- and polyamines and an aqueous phase;

d) separating distillatively water and aniline from the organic phase containing di- and polyamines,
   wherein
   d1) the distillation in step d) involves at least one pre-evaporation stage and at least one distillation stage,
   d2) aniline and water are partially separated off in the pre-evaporation stage from the organic phase containing di- and polyamines by flash evaporation, and
   d3) in the subsequent distillation stage, aniline and water remaining are separated off and di- and polyamines containing less than 1,000 ppm of water and less than 200 ppm of aniline, based on the weight of the di- and polyamines, are obtained; and e) subsequently cooling the di- and polyamines containing less than 1,000 ppm of water and less than 200 ppm of aniline.

In step e), cooling of the di- and polyamines containing less than 1,000 ppm of water and less than 200 ppm of aniline takes place preferably by heat exchange with the organic phase obtained in step c) containing di- and polyamines before or during the distillation thereof in step d), particularly preferably before or during the flash evaporation in the pre-evaporation stage (step d2)).

The mixture of aniline and water obtained in step d3) as distillate preferably contains less than 0.5 wt. % of di- and polyamines, based on the weight of the aniline or the aniline content in the mixture. Aniline is preferably separated off from this mixture of aniline and water and thereby an aniline containing less than 0.5 wt. % of di- and polyamines is obtained.

Cooling of the di- and polyamines containing less than 1,000 ppm of water and less than 200 ppm of aniline preferably takes place in step e) substantially directly after leaving the distillation in step d). The dwell time of the di- and polyamines containing less than 1,000 ppm of water and less than 200 ppm of aniline after leaving the distillation (step d)) at a temperature of 180° C. or more is preferably less than 30 minutes, more preferably less than 10 minutes.

The present invention also provides a process for the production of di- and polyisocyanates of the diphenylmethane series in which di- and polyamines are produced in accordance with the process according to the invention and reacted with phosgene to the corresponding di- and polyisocyanates. Such phosgenation can be carried out in accordance with a process known from the prior art (e.g. DE-A-844 896 or DE-A-198 17 691).

The acid-catalyzed condensation of aniline and formaldehyde in step a) can be carried out in accordance with a process known form the prior Art. Preferably aniline and aqueous formaldehyde solution at molar ratios in the range of 1.7:1 to 20:1, more preferably 1.7:1 to 5:1 are condensed in the presence of an acid catalyst, preferably a strong mineral acid such as hydrochloric acid, using 0.001 to 0.9, preferably 0.08 to 0.5 mol mineral acid per mole aniline. As can be appreciated by those skilled in the art, solid acid catalysts as described in the literature can also be used. The formaldehyde can thereby be introduced into a mixture of aniline and acid catalyst and the reaction solution reacted out by stage-wise heating. Alternatively, aniline and formaldehyde can also first of all be pre-reacted and mixed with the acid catalyst or a mixture of further aniline and acid catalyst, after which the reaction solution is reacted out by stage-wise heating.

This reaction can be performed continuously or discontinuously in accordance with one of the numerous processes described in the literature.

In step b), the reaction mixture containing the di- and polyamines is neutralized optionally with addition of water and/or aniline. Neutralization preferably takes place with sodium hydroxide solution.

The neutralized reaction mixture containing the di- and polyamines is separated in step c) into an organic phase containing di- and polyamines and an aqueous phase. This can be supported by the addition of aniline and/or water. If the phase separation is supported by addition of aniline and/or water, then the addition thereof preferably takes place with intensive mixing in the neutralization. This mixing can take place in mixing sections with static mixers, in stirred tanks or series of stirred tanks or else in a combination of mixing sections and stirred tank. The neutralized reaction mixture diluted by addition of aniline and/or water is preferably fed to an apparatus which on the basis of its configuration and/or internals is particularly suitable for separation into an organic phase containing MDA and an aqueous phase. Florentine flasks are preferably used with plate packs supporting the coalescence of the two phases as internals.

Optionally, washing of the organic phase with water and further separation of the water phase to remove residual contents of salt (DE-A-2549890) can follow.

In step d), water and aniline are separated off distillatively from the organic phase obtained in step c) containing di- and polyamines. The organic phase obtained in step c) preferably has a composition, based on the weight of the mixture, of 5-15 wt. % water and, depending on the proportions of aniline and formaldehyde used, preferably 5-90 wt. %, more preferably 5-40 wt. % aniline and preferably 5-90 wt. %, more preferably 50-90 wt. %, di- and polyamines. After leaving the phase separation in step c), the organic phase containing di- and polyamines preferably has a temperature of 80-150° C.

Among the features of the process according to the invention:

d1) the distillation in step d) involves at least one pre-evaporation stage followed by at least one distillation stage, and d2) aniline and water are partially separated off in the pre-evaporation stage from the organic phase containing di- and polyamines by flash evaporation, and d3) in the subsequent distillation stage, remaining aniline and water are separated off, such that di- and polyamines containing less than 1,000 ppm of water and less than 200 ppm of aniline, based on the weight of the di- and polyamines, are obtained. In the distillation stage, di- and polyamines with water contents of less than 500 ppm, particularly preferably of less than 300 ppm, based on the weight of the di- and polyamines, are preferably obtained. In the distillation stage, di- and polyamines with aniline contents of less than 50 ppm, particularly preferably of less than 20 ppm, based on the weight of the di- and polyamines, are preferably obtained. It is thereby advantageous to reduce the contents of water and aniline in the di- and polyamines as far as possible.

In step e), the di- and polyamines containing less than 1,000 ppm of water and less than 200 ppm of aniline are cooled. This takes place preferably by heat exchange with the organic phase containing di- and polyamines before or during the distillation thereof in step d), preferably before or during the flash evaporation thereof before or during step d2). Cooling can however also take place through a cooling medium.

The distillation in step d) of the process according to the invention is explained in more detail below by reference to the figures.

FIG. 1 shows a process flowchart of a single-stage distillation in which step d) of the process according to the invention cannot be carried out. The stream 4 of the organic phase obtained in step c) containing di- and polyamines is delivered to the head of a distillation column 1 with bottoms reboiler 2 and condenser 3. The distillation column 1 is operated at a head pressure of 2-100 mbar, preferably 5-50 mbar and a bottoms temperature of 200-300° C., preferably 220-270° C. and a vapor temperature of 20-200° C., preferably 50-150° C. The column has advantageously 2 to 20, preferably 3 to 10, theoretical separation stages which are formed by internals known from the prior art such as separation trays or packing, preferably by ordered packings. Any heat transfer equipment such as e.g. circulation evaporators, falling-film evaporators or tube bundles can be used as bottoms evaporator 2. They are operated by heating steam or other heat transfer media, corresponding to the bottoms temperature to be achieved. The product stream 5 (di- and polyamines) is taken from the bottoms or from evaporator 2 and advantageously cooled to a temperature of preferably 80-180° C., more preferably 90-150° C., most preferably 100-120° C. The separated water-aniline mixture 6 is condensed in the head condenser 3. Depending on the condensation temperature, known condensers such as air condensers, water-cooled or brine-cooled heat exchangers, optionally even several in series, can be used as head condenser. The condensation temperature required is given by the selected pressure. The condensate 7 is returned to the process from the condenser 3, residual gases 8 are led off, for example, via a vacuum system as waste gas.

The advantage of this system is its simplicity. A disadvantage, however, is the high bottoms temperature which can cause decomposition of the polyamine, and/or the low pressure required which results in large columns and costly condensation media. Also a disadvantage is the high consumption of heat at high temperature level.

Figure 2A:
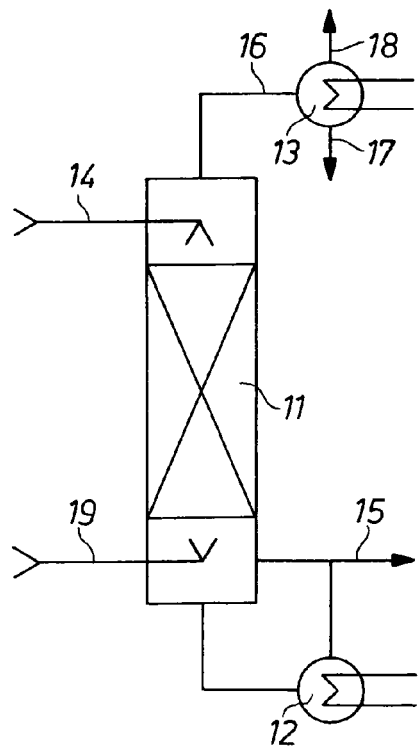
FIG. 2a illustrates a process flowchart of a single-stage distillation with steam feed.
Figure 2B:
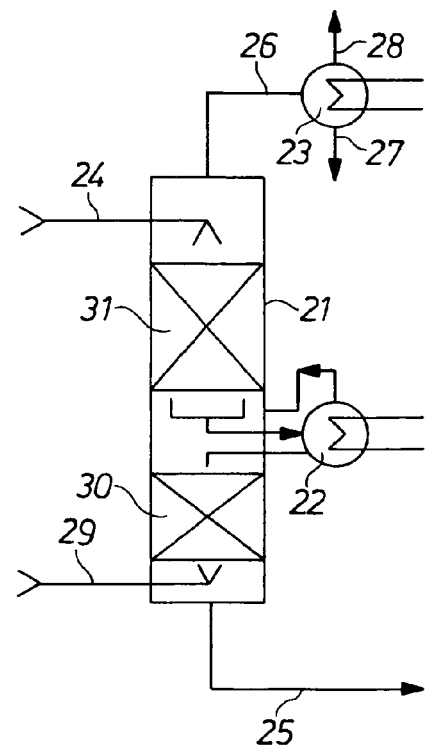
FIG. 2b depicts a process flowchart of a single-stage distillation with steam feed in which separation stages are arranged between the evaporator and the steam feed.

In an alternative embodiment of the single-stage distillation in which step d) of the process according to the invention cannot be carried out, the distillation is operated with steam feed. This embodiment is shown in FIGS. 2a and 2b. In FIGS. 2a and 2b, the stream 14 or 24 of the organic phase obtained in step c) containing di- and polyamines is delivered to the head of a distillation column 11, 21 into which steam is introduced in the bottoms (steam distillation). The distillation column is preferably operated at an absolute pressure of 20-1000 mbar, more preferably 50-200 mbar, a bottoms temperature of 120-300° C., more preferably 180-260° C. and a vapor temperature of 60-200° C., more preferably 80-150° C. The column 11, 21 has preferably 2 to 20, more preferably 3 to 10, theoretical separation stages which are formed by internals known from the prior art such as separation trays or packings, preferably by ordered packings. In the bottoms of the column 11, 21, steam is added as stream 19, 29 at a temperature of preferably 80-350° C., more preferably 100-250° C. In a preferred embodiment, the column 11 has an additional bottoms evaporator 12. In this case, a quantity of 10-200 kg steam/t di- and polyamines, preferably 20-100 kg/t is required. Any heat transfer equipment such as e.g. circulation evaporators, falling-film evaporators or tube bundles can be used as bottoms evaporator 12. They are operated with heating steam or other heat transfer media, according to the bottoms temperature to be achieved.

The column can also be operated without additional bottoms evaporator 12, though a quantity of steam of 1-10 t steam/t di- and polyamines product at a temperature of 280-350° C. is required.

The bottoms product (di- and polyamines) is removed in the bottoms of the column as stream 15, 25 and advantageously cooled to a temperature of 80-180° C., preferably 90-150° C., particularly preferably 100-120° C. The water-aniline mixture separated off 16, 26 is condensed in the head condenser 13, 23. Usual condensers which naturally must condense, in addition to the water and aniline from the raw solution, the added steam 19, 29, can however be used as head condenser. Known condensers such as air condensers, water-cooled or brine-cooled heat exchangers, optionally also several in series, can also be used as head condenser. The required condensation temperature is however given by the pressure selected. The condensate 17, 27 is returned to the process from the condenser 13, 23, residual gases 18, 28 are preferably led off via a vacuum system as waste air.

In a preferred variation of this second embodiment which is shown in FIG. 2 b, steam feed 29 and evaporator 22 are arranged on the column 21 such that some of the separation stages 30 of the column are located between the two. The liquid is passed to the upper part of the column internals 31 with at least 1-5 theoretical separation stages and passed via the evaporator 22 whereby vapor and liquid from there is led back into the column. This additional evaporator can be installed in the column e.g. as a circulation evaporator, falling-film evaporator or tube bundle or connected to the column as external evaporator by appropriate liquid offtakes from the column and return lines for the vapor and liquid.

After leaving the evaporator, the liquid is led to the lower part of the column internals 30 under which the steam feed 29 is introduced. The separation stages 31 of the column which also correspond to 2 to 20, preferably 3 to 10 theoretical trays and are achieved by internals known from the prior art, are therefore divided into two beds, wherein the upper bed preferably has 10 to 70% of the total separation stages, but at least one separation stage.

The advantage of the embodiments explained by means of FIGS. 2a and 2b compared with the embodiment shown in FIG. 1 is the lower bottoms temperature or the possible higher pressure which allows the use of smaller columns and allows condensation with air or water. A disadvantage, however, is the large quantity of vapor condensate produced and water occurring, the high consumption of heat at high temperature level and a high water content in the bottoms product.

To further reduce the water content in the bottoms product, this can suitably be re-treated by heating and optionally stripping with inert gas.

The process according to the invention therefore has in step d) an at least two-stage distillation step which has a pre-evaporation stage with flash evaporation and a subsequent distillation stage, and in which the energy content of the streams is used for heating or cooling, which is naturally particularly advantageous in large plants and/or high aniline and water contents in the raw solutions obtained in step c).

One, two or more pre-evaporation steps can thereby be provided, optionally also as stage distillation with use of vapor. It has proved particularly advantageous to use the heat content of the bottoms product leaving the distillation column (di- and polyamines containing less than 1,000 ppm of water and less than 200 ppm of aniline) as energy source for such a pre-evaporation stage, whereby at the same time the bottoms product (di- and polyamines containing less than 1,000 ppm of water and less than 200 ppm of aniline) is cooled. By coordinating these pre-evaporation steps, above all using low-quality energy (waste heat and low temperature level), the use of high-quality energy (heat at high temperature level) may be substantially reduced to achieve the product according to the invention. Ultimately, the pre-evaporation stages contained in the process according to the invention may considerably relieve the distillation column so that only substantially smaller columns are required or existing columns can achieve substantially higher capacity based on the di- and polyamines.

FIG. 3 shows a process flowchart of a two-stage distillation of the organic phase obtained in step c) containing di- and polyamines involving a pre-evaporation (flash evaporation) with feed of additional external energy in which step d) of the process according to the invention can be carried out. FIG. 3 shows a distillation column 31 which may preferably be arranged like one of the distillation columns shown in FIGS. 1, 2a or 2b with an evaporator and a condenser. Pre-evaporation by flash evaporation is carried out in apparatus 32. Pre-evaporation by flash evaporation takes place using the heat content of the organic phase containing di- and polyamines. Evaporation of the vapor stream 37 takes place with simultaneous cooling of the stream 34 of the organic phase containing the di- and polyamines. Pre-evaporation is however preferably operated with feed of additional external energy 39.

The pre-evaporation stage preferably includes a heat exchanger and vapor-liquid separator, wherein the vapor-liquid separation can also take place at the head of the subsequent distillation column. In the pre-evaporation stage, preferably 40-99.9 wt. %, more preferably 85-99 wt. % of the water content and preferably 2-90 wt. %, more preferably 10-80 wt. % of the aniline content of the stream 34 of the organic phase containing di- and polyamines is evaporated. It may be operated with feed of waste heats such as e.g. hot water at e.g. 80-110° C. or, preferably, with heating steam preferably at 1.1 to 20, more preferably 1.2 to 6 bar pressure and at a temperature of preferably 40 to 200° C., more preferably 80 to 140° C. and a pressure of preferably 20-2,000 mbar, more preferably 50-200 mbar. The feed stream 34 (organic phase containing di- and polyamines) is fed to the apparatus 32 for flash evaporation which is additionally heated with heat carriers (heating medium to feed additional external energy) 39.

The pre-evaporated stream 35 of the organic phase containing di- and polyamines with a remaining water content of 0.01-9 wt. %, preferably 0.1-2 wt. % and aniline content of 0.5-90 wt. %, preferably 1-35 wt. %, each based on the weight of the pre-evaporated organic phase containing di- and polyamines, is fed to the distillation column 31 and there separated into the bottoms product (stream 36 of the di- and polyamines containing less than 1,000 ppm of water and less than 200 ppm of aniline) and the vapor stream 38. The stages 31 and 32 can be operated at different or the same pressure. The vapor streams 37 and 38 can be processed separately or, above all at the same pressure, also jointly, usually by condensation.

FIG. 4 shows a process flowchart of a two-stage distillation of the organic phase obtained in step c) containing di- and polyamines comprising a pre-evaporation (flash evaporation) with feed of waste heat from the distillation in which step d) of the process according to the invention can be carried out. Thus, the heat content of the product stream produced (stream of the di- and polyamines containing less than 1,000 ppm of water and less than 200 ppm of aniline) may be used as an energy source for heating the flash evaporation and is cooled at the same time. FIG. 4 shows a distillation column 41 which is arranged like one of the distillation columns shown in FIGS. 1, 2a or 2b containing an evaporator and a condenser.

Pre-evaporation by flash evaporation may carried out in apparatus 42 containing a heat exchanger and a vapor-liquid separator. In the pre-evaporation, preferably 50-99.5 wt. %, more preferably 70-98.5 wt. % of the water content and preferably 2-90 wt. %, more preferably 5-70 wt. % of the aniline content from the stream 44 of the organic phase obtained in step c) containing di- and polyamines may evaporated. The pre-evaporation is operated in product terms preferably at a temperature of 50-180° C., more preferably 60-120° C., and an absolute pressure of preferably 20-2000, more preferably 50 to 200 mbar. The pre-evaporated stream 45 of the organic phase containing di- and polyamines with a remaining water content of preferably 0.03-7 wt. %, more preferably 0.1-3 wt. %, and aniline content of preferably 3-90 wt. %, more preferably 5-38 wt. %, based respectively on the weight of the stream 45, is fed to the distillation column 41 and there separated into the bottoms product (stream 49 of the di- and polyamines containing less than 1,000 ppm of water and less than 200 ppm of aniline) and the vapor stream 48.

The hot bottoms product 49 with a product temperature of preferably 120-300° C., more preferably 180-260° C., is fed as heating agent to the heat exchanger of apparatus 42 of the pre-evaporation stage, where it is cooled by preferably 20-200° C., more preferably 60-160° C. and is led off as cooled bottoms product 46 at a temperature of preferably 80-180° C., more preferably 90-150° C., most preferably 100-120° C. Stages 41 and 42 may be operated at different or the same pressure. The vapor streams 47 and 48 may be processed separately or, above all at the same pressure, also jointly, usually by condensation.

FIG. 5 shows a process flowchart of a three-stage distillation including a two-stage flash evaporation with feed of additional external energy and with feed of waste heat from the distillation, in which step d) of the process according to the invention can be carried out.

The first pre-evaporation stage 52 may be a pure flash evaporation with exclusive use of the heat content of the stream 54 of the organic phase obtained in step c) containing di- and polyamines, but as shown in FIG. 5 may preferably be operated with feed of additional external energy. The external energy may be for example low-pressure steam or other forms of preferably low-quality energy such as e.g. hot water. In the second pre-evaporation stage 53, the heat content of the product stream obtained from distillation column 51 (stream 59 of the di- and polyamines containing less than 1,000 ppm of water and less than 200 ppm of aniline) is used as energy source for the further flash evaporation of the stream 55 obtained from the first pre-evaporation stage 52 of the pre-evaporated organic phase containing di- and polyamines.

The distillation stage 51 shown in FIG. 5 may preferably be arranged as one of the distillation columns shown in FIGS. 1, 2a or 2b containing an evaporator and a condenser. The pre-evaporation stage 52 is however a pre-evaporation stage which preferably includes a heat exchanger and a vapor-liquid separator. In the pre-evaporation stage 52, preferably 40-99.9 wt. %, more preferably 85-99 wt. % of the water content and preferably 2-90 wt. %, more preferably 10-80 wt. % of the aniline content which is contained in the stream 54 of the organic phase obtained in step c) containing di- and polyamines, may be evaporated. The feed 54 of the organic phase containing di- and polyamines is fed to the pre-evaporation stage 52 which may be operated with a stream 61 of a heating medium (preferably waste heat such as e.g. hot water at e.g. 80-110° C. or heating steam at 1.1 to 20, preferably 1.2 to 6 bar pressure) and in product terms at a temperature of preferably 40 to 160° C., more preferably 80 to 105° C., and an absolute pressure of preferably 20-2000 mbar, more preferably 50 to 200 mbar. Removal of the cooled stream of the heating medium is not shown in FIG. 5.

The pre-evaporated stream 55 of the organic phase containing di- and polyamines with a remaining water content of preferably 0.01-9 wt. %, more preferably 0.1-2 wt. %, and aniline content of preferably 0.5-90 wt. %, more preferably 5-35 wt. %, based respectively on the weight of the stream 55, is fed to the second pre-evaporation stage 53 preferably containing a heat exchanger and a vapor-liquid separator. It may be operated in product terms at a temperature of preferably 100-200° C., more preferably 130-180° C., and an absolute pressure of preferably 20-2000 mbar, more preferably 50 to 200 mbar. The pre-evaporated stream 60 thus obtained of the organic phase containing di- and polyamines with a water content of preferably 50-500 ppm and an aniline content of preferably 1-20 wt. %, more preferably of 3-12 wt. %, based respectively on the weight of the stream 60, is fed to the distillation column 51 and there separated into the bottoms product (stream 59 of the di- and polyamines containing less than 1,000 ppm of water and less than 200 ppm of aniline) and the vapor stream 58. The hot stream 59 of the bottoms product with a temperature in product terms of preferably 120-300° C., particularly preferably 180-260° C. may be fed as heating agent to the heat exchanger of the second pre-evaporation stage 53 where it is cooled by 20-180° C. and led off as cooled bottoms product 56 (di- and polyamines) at a temperature of preferably 80-180° C., more preferably 90-150° C., most preferably 100-120° C. Stages 51, 52 and 53 may be operated at different or the same pressure. The vapor streams 82, 57 and 58 may be processed separately or, above all at the same pressure, also jointly, usually by condensation.

FIG. 6 shows a process flowchart for a three-stage distillation including a flash evaporation with feed of waste heat from the distillation and with feed of additional external energy, in which stage d) of the process according to the invention can be carried out.

The first pre-evaporation stage 62 is a pure flash evaporation which is operated using the heat content of the bottoms product obtained in the distillation from the distillation column 73 (stream 69 of the di- and polyamines containing less than 1,000 ppm of water and less than 200 ppm of aniline) by heat exchange. In the second pre-evaporation stage 63, external energy is used as energy source for the further flash evaporation. The external energy may for example be low-pressure steam or other forms of preferably low-quality energy such as e.g. hot water.

The distillation stage 73 shown in FIG. 6 may preferably be arranged like one of the distillation columns shown in FIGS. 1, 2a or 2b containing an evaporator and a condenser. The pre-evaporation stage 62 is however a pre-evaporation stage preferably including a heat exchanger and a vapor-liquid separator. In the pre-evaporation stage 62, preferably 60-99 wt. % of the water content and up to 80 wt. %, of the aniline content which is contained in the stream 64 of the organic phase obtained in step c) containing di- and polyamines, may be evaporated.

The operation may be carried out in product terms at a temperature of preferably 40 to 180° C., more preferably 50 to 110° C., and an absolute pressure of preferably 20-2000 mbar, more preferably 50 to 200 mbar. The feed 64 of the organic phase containing di- and polyamines is fed to the pre-evaporation stage 62, there pre-evaporated, and the stream 65 obtained of the pre-evaporated organic phase containing di- and polyamines with a water content of preferably 0.5-9 wt. %, more preferably 0.1-2 wt. %, and an aniline content of preferably 2-80 wt. %, more preferably 10-35 wt. %, based respectively on the weight of the stream 65, fed to the second pre-evaporation stage 63. The second pre-evaporation stage 63 preferably includes a heat exchanger and a vapor-liquid separator. It is preferably operated with a stream 71 of a heating medium (preferably waste heat such as e.g. hot water at e.g. 80-110° C. or heating steam at 1.1 to 20, preferably 1.2 to 6 bar pressure) and in product terms at a temperature of preferably 100 to 200° C., more preferably 130 to 180° C., and an absolute pressure of preferably 20 to 2000 mbar, more preferably 50 to 200 mbar. Removal of the cooled stream of the heating medium is not shown in FIG. 6.

The pre-evaporated stream 70 of the organic phase containing di- and polyamines from the second pre-evaporation stage 63 with a water content of preferably less than 1 wt. %, particularly preferably 100 to 800 ppm and an aniline content of preferably 1-50 wt. %, particularly preferably 4 to 20 wt. %, based respectively on the weight of the stream 70, may be fed to the distillation column 73 and there separated into the bottoms product (stream 69 of the di- and polyamines containing less than 1000 ppm of water and less than 200 ppm of aniline) and the vapor stream 68. The hot bottoms product 69 at a temperature of preferably 120-300° C., particularly preferably 180-260° C., may be fed as heating medium to the heat exchanger of the first pre-evaporation stage 62 where it is cooled by preferably 20-180° C. and led off as cooled bottoms product 66 at a temperature of preferably 80-180° C., more preferably 90-150° C., most preferably 100-120° C. The stages 62, 63 and 73 may be operated at different or the same pressure. The vapor streams 72, 67 and 68 may be processed separately or, above all at the same pressure, also jointly, usually by condensation.

In the embodiments described in which step d) of the process according to the invention can be carried out, the mixture of di- and polyamines of the diphenylmethane series with water contents of under 1,000, preferably under 500 and particularly preferably under 300 ppm, and aniline contents of under 200, preferably under 50, especially preferably under 20 ppm, based on the weight of the mixture of di- and polyamines, is obtained with a varying level of energy input as bottoms product.

The present invention is further illustrated, but is not to be limited, by the following examples.

EXAMPLES

Example 1

Production of the Organic Phase Containing Di- and Polyamines (Steps a) to c))

2,600 g aniline were mixed intensively with stirring at 25° C. with 1000 g formalin (30 wt. % aqueous solution of formaldehyde) in a stirred tank, in which the mixture was heated to 60° C. The stirrer was stopped and the water phase separating off above was removed. 680 g 30 wt. % aqueous hydrochloric acid was added with renewed stirring and cooling, wherein a temperature of 45° C. was maintained. After 15 minutes' further stirring at this temperature, cooling was replaced by heating and the mixture evenly heated to 140° C. over a period of 120 minutes at 5 bar pressure and kept at this temperature for 15 minutes.

The mixture was cooled to 100° C., reduced to normal pressure and neutralized by addition of 540 g 50 wt. % aqueous sodium hydroxide solution with stirring. After stopping the stirrer, the phases were left to settle out and the lower salt water phase siphoned off. The organic phase was mixed at 100° C. with 300 g water, the phases again left to separate and the water phase floating on top separated off. 3,005 g of the organic phase containing di- and polyamines at 100° C. were obtained, of the following composition:

1160 g=39 wt. % diaminodiphenylmethane (binuclear MDA, diamine-isomer mixture)
600 g=20 wt. % polyamines (tri- and higher-nuclear MDA)
935 g=31 wt. % aniline
310 g=10 wt. % water

Comparative Example 2

Not According to the Invention

Processing of the Organic Phase Containing Di- and Polyamines (Without Pre-Evaporation)

An apparatus according to FIG. 2b consisting of a column 21 with a diameter of 80 mm, an upper bed with a MEL-LAPAK 250X structured packing 1659 mm in height (4 theoretical separation stages), a falling-film evaporator located under this and heated with 30 bar steam and a lower bed with a MELLAPAK 250X structured packing 1659 mm in height (4 theoretical separation stages) was used. The column was operated at 60 mbar. The organic phase obtained in Example 1 containing di- and polyamines was delivered to the column at 400 g/min and heated to 220° C. in the evaporator, wherein water and aniline were distilled off. 12 g/min steam, at a temperature of 230° C., were fed under the lower bed. The vapors were condensed on a condenser cooled with water. The bottoms product leaving the column at 205° C. was cooled to 100° C. by water cooling and had a water content of 285 ppm and an aniline content of 12 ppm. The consumption of heating steam at 30 bar was 490 g/kg product (di- and polyamines).

Example 3

According to the Invention

Processing of the Organic Phase Containing Di- and Polyamines (with Pre-Evaporation)

An apparatus according to FIG. 5 made from a first pre-evaporation stage 52 containing a heat exchanger which was heated with 1.5 bar steam (waste heat e.g. from the pressure relief of 30 bar steam condensate), and a gas-liquid separator; a second pre-evaporation stage 53 containing a heat exchanger which was heated with the hot product discharge from the distillation column 51, and a gas-liquid separator; and distillation column 51 with a diameter of 80 mm, an upper bed with a MELLAPAK 250X structured packing 1659 mm in height (4 theoretical separation stages), a falling-film evaporator located under it heated with 30 bar steam and a lower bed with a MELLAPAK 250X structured packing 1659 mm in height (4 theoretical separation stages), was used. The first pre-evaporation stage 52 was operated at 80 mbar absolute pressure, the second pre-evaporation stage 53 at 70 mbar absolute pressure and the distillation column 51 at 60 mbar absolute pressure. The organic phase obtained in Example 1 containing di- and polyamines was introduced into the first pre-evaporation stage 52 at 1600 g/min, wherein a temperature of 97° C. was set. The bottoms from the separator of this stage flowed into the second pre-evaporation stage 53 in which a temperature of 141° C. was set. The bottoms from the separator of this stage was delivered to the distillation column 51 and heated in the evaporator to 220° C., wherein remaining water and aniline were distilled off. 47 g/min steam at a temperature of 120° C. were fed under the lower bed. The vapors of all three stages were condensed separately on condensers cooled with water. The condensate contained, based on the aniline content, 0.13 wt. % MDA. The bottoms product leaving the column at 210° C. was cooled to 118° C. by the heat exchanger of the second pre-evaporation stage 53 and had a water content of 285 ppm and an aniline content of 12 ppm. The consumption of heating steam at 30 bar pressure was 120 g/kg product (di- and polyamines), the consumption of heating steam at 1.5 bar pressure (waste heat) 230 g/kg product (di- and polyamines).

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A process for the production of di- and polyamines of the diphenylmethane series comprising:

a) reacting aniline and formaldehyde in the presence of an acid catalyst to produce a reaction mixture containing di- and polyamines;

b) neutralizing the reaction mixture containing di- and polyamines;

c) separating the neutralized reaction mixture containing di- and polyamines into an organic phase containing di- and polyamines and an aqueous phase;

d) separating by distillation the water and aniline from the organic phase containing di- and polyamines;

wherein d1) the distillation in step d) comprises at least one pre-evaporation stage and at least one distillation stage, d2) aniline and water are partially separated off in the pre-evaporation stage from the organic phase containing di- and polyamines by flash evaporation, and d3) in the subsequent distillation stage, the remaining aniline and water are separated off, such that di- and polyamines containing less than about 1,000 ppm of water and less than about 200 ppm of aniline, based on the weight of the di- and polyamines, are obtained and e) cooling the di- and polyamines containing less than about 1,000 ppm of water and less than about 200 ppm of aniline.

2. The process according to claim 1, wherein the cooling of the di- and polyamines containing less than about 1,000 ppm of water and less than about 200 ppm of aniline in step e) takes place by heat exchange with the organic phase containing di- and polyamines before or during the distillation thereof in step d).

3. The process according to claim 1, wherein the pre-evaporation of the organic phase containing di- and polyamines in step d2) takes place by at least a two-stage flash evaporation and with feed of heat which is exchanged by heat exchange of the organic phase containing di- and polyamines with the stream of di- and polyamines containing less than about 1,000 ppm of water and less than about 200 ppm of aniline.

4. The process according to claim 1, wherein the mixture of aniline and water obtained in step d3) as distillate contains less than about 0.5 wt. % of di- and polyamines, based on the weight of the aniline.

5. The process for the production of di- and polyisocyanates of the diphenylmethane series, wherein di- and polyamines are produced according to the process of claim 1 and reacted with phosgene to the corresponding di- and polyisocyanates.

* * * * *